(12) United States Patent
Murray et al.

(10) Patent No.: US 7,189,886 B2
(45) Date of Patent: Mar. 13, 2007

(54) PROCESS FOR PRODUCING ALKYLBENZENE

(75) Inventors: Brendan Dermot Murray, Houston, TX (US); Garo Garbis Vaporciyan, Houston, TX (US)

(73) Assignee: Shell Oil Company, Houston, TX (US)

( * ) Notice: Subject to any disclaimer, the term of this patent is extended or adjusted under 35 U.S.C. 154(b) by 485 days.

(21) Appl. No.: 10/880,072

(22) Filed: Jun. 29, 2004

(65) Prior Publication Data

US 2005/0054890 A1 Mar. 10, 2005
US 2006/0189836 A9 Aug. 24, 2006

Related U.S. Application Data

(60) Provisional application No. 60/483,671, filed on Jun. 30, 2003.

(51) Int. Cl.
C07C 1/20 (2006.01)
(52) U.S. Cl. .................. 585/469; 203/DIG. 6
(58) Field of Classification Search ............ 585/469; 203/DIG. 6
See application file for complete search history.

(56) References Cited

U.S. PATENT DOCUMENTS

| | | | |
|---|---|---|---|
| 4,232,177 A | 11/1980 | Smith, Jr. | 585/324 |
| 4,242,530 A | 12/1980 | Smith, Jr. | |
| 4,443,559 A | 4/1984 | Smith, Jr. | |
| 4,822,936 A | 4/1989 | Maurer et al. | |
| 5,266,546 A | 11/1993 | Hearn | |
| 5,348,710 A | 9/1994 | Johnson et al. | |
| 5,475,159 A | 12/1995 | Singleton et al. | |
| 5,905,178 A | 5/1999 | Hildreth | 585/258 |
| 6,455,712 B1 | 9/2002 | Vaporciyan et al. | |

FOREIGN PATENT DOCUMENTS

| | | |
|---|---|---|
| GB | 1122702 | 8/1968 |
| WO | 01/70714 | 9/2001 |
| WO | 02/48125 | 6/2002 |
| WO | 02/48126 | 6/2002 |
| WO | 02/48127 | 6/2002 |

OTHER PUBLICATIONS 2001607516, 2001, Derwent abstract.
2001590165, 2001, Derwent abstract.
2001590164, 2001, Derwent abstract.
2001590161, 2001, Derwent abstract.
2001159501, 2001, Derwent abstract.
International Search Report. dated Jan. 13, 2005.

*Primary Examiner*—Thuan Dinh Dang

(57) ABSTRACT

A process for producing an alkylbenzene from an alkylphenyl alcohol involving the steps of:
(a) feeding a feed stream containing alkylphenyl a reactor having a catalytic distillation zone; and,
(b) concurrently in the reactor
  (i) contacting the feed stream containing alkylphenyl alcohol with hydrogen in the catalytic distillation zone to convert alkylphenyl alcohol to alkylbenzene over a catalyst containing Group VIII or a Group IB metal; and,
  (ii) separating alkylbenzene from the reaction mixture by fractional distillation to produce an overhead stream containing alkylbenzene having a reduced concentration of alkylphenyl alcohol than the feed stream from the distillation column reactor.

Examples of the alkylphenyl alcohol include cumyl alcohol, phenyl ethyl alcohol, or di(2-hydroxyl 2-propyl)benzene, and that for the alkylbenzene include cumene and di-ethyl benzene, or di(2-hydroxyl-2-propyl)benzene.

18 Claims, 1 Drawing Sheet

PROCESS FOR PRODUCING ALKYLBENZENE

This application claims the benefit of U.S. Provisional Application No. 60/483,671 filed Jun. 30, 2003.

FIELD OF THE INVENTION

The present invention relates to a process for preparing alkylbenzene from alkylaryl alcohol. Particularly, the present invention relates to a process for preparing cumene from cumyl alcohol.

BACKGROUND OF THE INVENTION

It is known that alkylbenzenes can be generated from alkylaryl alcohols by a process involving dehydration and hydrogenolysis. Substantial quantities of undesirable side products are usually generated from further reaction of alkylbenzene during the process.

It is also known that cumene (isopropylbenzene) can be generated from cumyl alcohol (2-phenyl-2-propanol) by a multiple-step process which involves dehydration to α-methyl styrene followed by the hydrogenation to cumene by a hydrogenolysis fixed-bed reaction, and the subsequent fractional distillation step to recover cumene. Substantial quantities of i-propylcyclohexane and cumene dimer are produced as undesirable by-products because alpha-methylstyrene ("AMS") and cumene can stay on the hydrogenation bed after they are produced, (before exiting the catalyst bed) resulting in the further hydrogenation or dimerization thereof.

U.S. Pat. No. 6,455,712, WO 02/48126, WO 02/48125, and WO 02/48127 assigned to Shell Oil Company, disclose a process for reacting an alkylaryl hydroperoxide(s), such as obtained from cumene or dialkyl aryl, with an olefin to obtain a product stream comprising an oxirane compound and an alkylaryl hydroxyl compound, such as cumyl alcohol (also known as 2-phenyl-2-propanol) or p-di-(2-hydroxy-2-propyl)benzene or 2-propyl-3(2-hydroxy-2-propyl)benzene. Alkylaryl hydroxyl compounds are dehydrated and hydrogenated to produce alkyl aryl(s), followed by fractional distillation to recover alkylaryls, such as cumene or dialkyl aryl. 0.1–10 wt. % of i-propylcyclohexane is produced as undesirable side product. It is difficult to separate this impurity from cumene by fractional distillation due to the proximity of their boiling points.

WO 01/70714, assigned to Sumitomo, describes a process relating to oxidizing cumene to obtain isopropylbenzene peroxide as an oxygen carrier for the epoxidation of propylene to produce propylene oxide and cumyl alcohol. The cumyl alcohol is dehydrated and hydrogenated, via a hydrogenolysis step, to cumene and recycled for repeated use. During the hydrogenolysis step, up to 5 wt % of cumene is dimerized to produce cumene dimer, an undesirable by-product.

It is therefore desirable to develop a more efficient process which combines the multiple-step process into fewer steps and yet selectively produces a more pure cumene product with a smaller quantity of undesirable by-products.

SUMMARY OF THE INVENTION

The present invention is directed to a process for producing an alkylbenzene having the structure of $R_1R_2CH(Ph)$ from an alkylphenyl alcohol (also known as alkylaryl alcohol) having the structure $R_1R_2C(Ph)OH$; wherein $R_1$, and $R_2$ each is hydrogen or a hydrocarbon group having 1–10 carbon atoms and at least one of $R_1$, and $R_2$ is not a hydrogen, wherein the process comprises the steps of:

(a) feeding a feed stream comprising alkylphenyl alcohol having the structure $R_1R_2C(Ph)OH$ to a reactor having a catalytic distillation zone;
(b) concurrently in the reactor
 (i) contacting the feed stream comprising $R_1R_2C(Ph)OH$ with hydrogen in the catalytic distillation zone to convert $R_1R_2C(Ph)OH$ to $R_1R_2C(Ph)H$ over a catalyst comprising Group VIII or a Group IB metal; and,
 (ii) separating $R_1R_2C(Ph)H$ from the reaction mixture (i) by fractional distillation to produce at a position upper from the catalytic distillation zone a stream comprising $R_1R_2C(Ph)H$ having a reduced concentration of $R_1R_2C(Ph)OH$ than the feed stream from the distillation column reactor as an overhead.

Non-limiting illustrative examples of the alkylaryl alcohol include cumyl alcohol, phenyl ethyl alcohol, and ortho, meta, or para-di-(2-hydroxyl 2-propyl)benzene, and that for the alkylbenzene include cumene, diethyl benzene, and meta, ortho, or para-di-(isopropyl)benzene.

BRIEF DESCRIPTION OF THE FIGURE

The FIGURE is a flow diagram in schematic form of an embodiment of the invention.

DETAILED DESCRIPTION OF THE INVENTION

Figure 1:
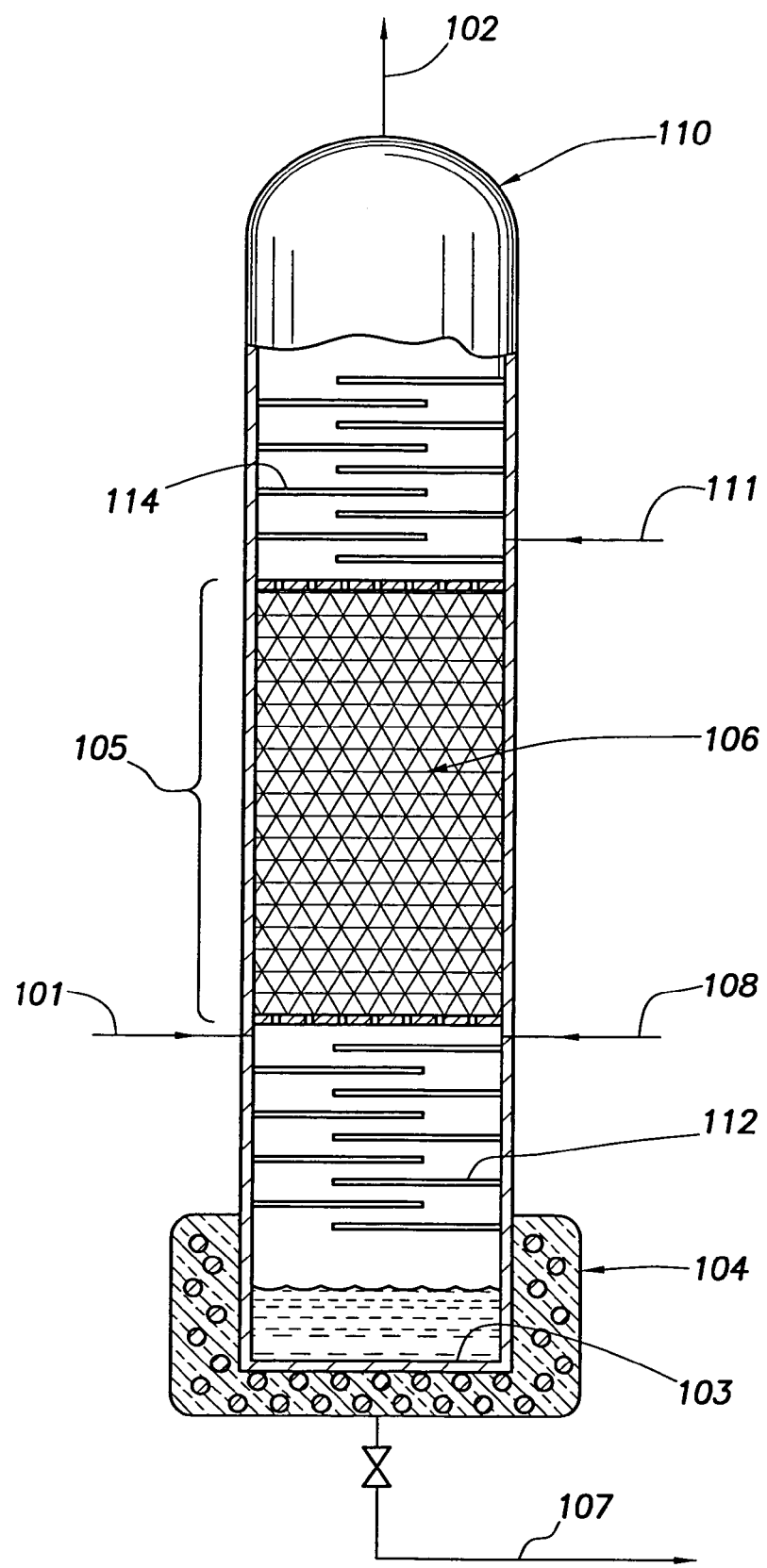

The present invention is directed to an improved process for converting an alkylphenyl alcohol to alkylbenzene. The FIGURE shows a simplified flow diagram in schematic of a catalytic distillation reaction embodiment. The process involves feeding alkylphenyl alcohol-containing feed stream 101 to a catalytic distillation reactor into a feed zone, contacting the alkylaryl alcohol-containing feed stream with a fixed bed catalytic packing 106 to concurrently carry out a one-step dehydration-hydrogenation reaction, fractionate and remove the lower boiling point alkylbenzene produced in the catalytic distillation zone by distillation before being converted to alkylcyclohexane or dimers of alkylphenyl alcohol, while unconverted alkylaryl alcohol or alkylaryl alcohol continue to be refluxed to the catalytic distillation zone 105 containing catalyst until they are converted to alkylbenzene. A heating device with heating media 104 can be utilized to provide the heat needed for the distillation reaction.

The catalytic distillation operation mode provides an advantage of enhancing the selectivity of the reaction to alkylbenzene, such as cumene, by continuously removing the product alkylbenzene through fractional distillation in the catalytic distillation reactor. The continuous catalytic distillation operations, with concurrent catalytic reaction and fractionation of product, benefit from the fact that the boiling points of the majority of alkylphenyl alcohols are higher than those for the corresponding product alkylbenzenes. The present invention provides further advantages by lowering the required capital expenditure through operating multiple dehydration and catalytic hydrogenolysis reactions as well as fractionation steps in a single reactor without a separate hydrogenation reactor with its accompanying heat exchange equipment and controls. The combination of catalytic distillation and the particular catalytic hydrogenation reaction results in a better selectivity toward the saturation of the alkenyl chain, produced from the dehydration of the alkylaryl alcohol, without hydrogenation of the aromatic bonds.

Without limiting the scope of the present invention, the alkylaryl alcohol may have a formulation of $R_1R_2C(Ph)OH$ and the alkylbenzene produced may have a structure of $R_1R_2C(Ph)H$ wherein $R_1$ and $R_2$ each is a hydrogen or a hydrocarbon group having 1–10 carbon atoms, and at least one of $R_1$ and $R_2$ is not a hydrogen.

As a specific embodiment of the present invention, the alkylaryl alcohol is cumyl alcohol and the alkylbenzene produced is cumene. Table 1 below shows that cumene has a lower boiling point than both cumyl alcohol and cumene dimers, which are 2,3-dimethyl-2,3-diphenylbutane and 2-methyl-2,4-diphenylpentane, etc. Therefore, cumene produced is recovered from the overhead 102 or side-draw above the catalyst bed 105 upper from the catalytic distillation zone, leaving unconverted cumyl alcohol in the catalyst bed 105 for reaction. Any cumene dimers, having the highest boiling points, stay in the bottom section of the reactor, and will not be distilled out of the top of the reactor. The mixture at the bottom of the reactor 103 which may contain cumene dimers, if any, can be withdrawn as a bottom stream 107.

TABLE 1

| Compound | Boiling Point at 1 Atm. Pressure, ° C. |
| --- | --- |
| cumyl alcohol | 201 |
| cumene | 152–154 |
| alpha-methylstyrene | 165–169 |
| iso-propylcyclohexane | 155 |
| 2-methyl-2,4-diphenylpentane | 300–320 |
| dimethyl-2,3-diphenylbutane | 300–320 |

In another specific embodiment of the present invention, the alkylaryl alcohol is cumyl alcohol and the alkylbenzene produced is cumene. The alkylaryl alcohol can also be ethylphenyl alcohol (also known as 1-hydroxyl-1-phenyl ethane or hydroxyethylbenzene) wherein the alkylbenzene produced is ethyl benzene. In still another specific embodiment of the present invention, the alkyaryl alcohol is ortho, meta, para-di-(2-hydroxyl-2-propyl)benzene, 4-(2-hydroxy-2-propyl)cumene, 3-(2-hydroxy-2-propyl)cumene, 2-(2-hydroxy-2-propyl)cumene, or mixtures thereof, resulting in the alkylbenzenes meta, ortho, para-di-(isopropyl) benzene, or mixtures thereof. Particularly, the alkyaryl alcohol is para-di-(2-hydroxyl-2-propyl)benzene and the alkylbenzene is para-di-(isopropyl)benzene.

As a particular embodiment of the present invention, less than about 1.0, particularly less than about 0.5, and more particularly less than about 0.2% by weight of the alkylbenzene produced is converted to alkyl cyclohexane ($R_1R_2CH$ (cyclohexane)), and less than about 0.1, particularly less than about 0.05, and more particularly less than 0.01% by weight of the alkylbenzene produced is converted to side products in the form of dimer(s) or polymer(s) of alkylbenzene.

As a particular embodiment, any heavy dimers or polymers of alkylbenzenes, such as cumene dimers, made in the catalytic distillation mode, having higher boiling points than alkylbenzenes and alkyaryl alcohols, fall to the bottom of the catalytic distillation reactor 103. The dimers or oligomers in the bottom of the reactor 103 may be withdrawn as a part of the bottom stream 107 and may optionally be subsequently hydrocracked, e.g., in a fixed bed mode, to produce more alkylbenzenes, such as cumene. Optionally, the bottom stream is fractionated to remove alkylphenyl alcohol, alkenylbenzene, and/or alkylbenzene, which are optionally recycled back to the catalytic distillation reactor, prior to being hydrocracked. Optionally, the dimers or oligomers can be hydrogenated/hydrocracked at the bottom of the reactor. Non-limiting illustrative examples of side product dimers made from dimerization of cumene include 2,3-dimethy-2, 3-diphenyl butane and 2-methyl-2,4-diphenylpentane. Illustrative and non-limiting examples of suitable hydrogenation or hydrocracking catalysts for converting dimers of alkylbenzenes to alkylbenzene, such as converting 2,3-dimethyl-2,3-diphenyl butane and 2-methyl-2,4-diphenylpentane to cumene include catalysts comprising Group VIII metal or Group IB metal on a support, particularly those comprising copper, palladium, platinum and nickel on a support. Non-limiting illustrative examples of support include silica, silica-alumina, and zeolite, such as Mordenite, Na/H-Mordenite, H-Mordenite, beta-zeolite, H-beta-zeolite, Y-zeolite, H—Y-zeolite, and the like. In one particular embodiment of the present invention, the catalysts contain from about 0.1 to about 5% wt., particularly from about 0.2 to 2% wt, calculated as the weight of the metal on the basis of the total weight of the catalyst, of Group VIII metal or a Group VIII metal compound as principal catalytic component, alone or with promoters and modifiers such as palladium/gold, palladium/silver, cobalt/zirconium, nickel, preferably deposited on ac support, preferably deposited on a support in acidic hydrogen form. The term of "acidic hydrogen form" means the 50% or more of ion exchangeable cations are hydrogen (+) ions (also known as "H$^+$" or "proton"). The Group IB metal-containing catalysts preferably contain from about 10% to about 80%, particularly from about 30% to about 70%, more particularly from about 50% to about 60%, as the weight of the oxide basis the total weight of the catalyst, of a Group IB metal, particularly on an acidic support, more particularly on a support in acidic hydrogen form. Specific non-limiting examples of such catalysts include catalysts comprising copper, Raney copper, copper/chrome, copper/zinc, copper/zinc/chrome, copper/zinc/zirconium, copper/silica, copper/zinc/aluminum copper/alumina, palladium/carbon, palladium/H-Mordenite and other copper-based catalyst systems. From about 86.0% to about 100.0%, particularly from about 90.0% to about 100.0%, more particularly from about 94.0% to about 100.0%, still more particularly from about 97.5% to about 100.0%, and still more particularly from about 98.0% to about 100.0% by weight of dimers of alkylbenzenes is converted to alkylbenzene at a temperature from about 140° C. to about 300° C., particularly from about 185° C. to about 235° C., and more particularly from about 185° C. to about 225° C.

As a non-limiting illustrative example, the catalytic distillation bed (also known as catalytic distillation zone having catalysts employed ) 105, the shaded area in the FIGURE, is positioned centrally in the catalytic distillation reactor at a point below the top 110 (where alkylbenzene is recovered as an overhead) or side draw of alkylbenzene product stream, the feed stream and the hydrogen-containing stream 108 is fed into the reactor below the catalytic distillation bed 105. This configuration allows the feed stream and hydrogen to move up into the bed and contact the catalyst under the conditions described herein to hydrogenate the side chain. In the alternative, the feed stream is fed into the catalytic distillation reactor 105 at above the catalytic distillation bed 105 and moves down into the catalytic distillation bed 105 and contacts the hydrogen fed from below the catalytic distillation bed 105. As still another alternative, the feed stream enters the reactor at the catalytic distillation zone 105. Not intended to limit the scope of the invention, one may design the entry point of the feed stream 101 into reactor according to the concentration of the feed stream, e.g. the higher the concentration of the alkylphenyl alcohol in the feed stream, the higher up will the entry point for the feed stream 101 be. A non-limiting illustrative example of a suitable catalytic distillation reactor has an outer diameter from about 0.01 meter to about 20 meters, and particularly from about 0.5 meter to about 10 meters; and a height from about 0.2 meter to about 200 meters, and particularly from about 1 meter to about 100 meters.

The catalytic distillation zone/bed 105 can be packed in any way to provide sufficient restriction for separation. A non-limiting illustrative example includes adding structured packings in addition to the catalyst material in the bed 105. The catalyst material may be shaped and sized in such as way as to impart improved efficiency in a manner achieved by conventional packed columns for fractional distillations, and thus functioning as both a catalyst and distillation packing. The catalyst packing is of such a nature as to allow the vapor flow through the catalytic distillation bed, yet provide a sufficient surface area for catalytic contact.

As a non-limiting illustrative example, the catalysts may be packed into a plurality of trays and maintained in a flooded state as the liquid in the reactor passes down through the trays to the next lower trays. The material may then be fractionated on the lower tray as in a conventional fractionation tower. Optionally, additional trays/packings 112 without catalyst may be employed below the catalytic distillation bed 105. These trays/packings may be below the entry point of hydrogen-containing feed stream 108 and/or below the entry point of the feed stream 101, and are designed to improve separation among the reactants and products, especially between alkylphenyl alcohol and alkylbenzene dimer(s)/oligomers thus reducing alkylphenyl alcohol content in the bottom of the reactor 103. The feed stream 101 containing higher boiling reactant alkylaryl alcohols, such as cumyl alcohol, is continually contacted with the catalyst loaded in the catalyst bed in a catalytic distillation reaction zone 105, and concurrently, the resulting reaction mixture is fractionated in the fixed bed catalyst; the lower boiling product alkylbenzenes, such as cumene, pass upward through the catalyst beds and may be recovered as a part (usually the majority) of the overhead or side draw above the catalyst bed. The hydrogenation reaction (coupled with dehydration) and fractionation occur concurrently over the fixed catalyst bed, which serves as both catalyst and distillation packing in the catalytic distillation reactor. The unreacted alkylphenyl alcohols and alkenylbenzenes are left behind in the catalyst bed and are in contact with the catalyst for conversion into alkylbenzene. Most of the alkylaryl alcohols are dehydrated to form alkenylbenzenes which only exist in transient, and are immediately hydrogenated to alkylbenzenes in the catalyst bed. Optionally, additional packings/trays 114 are employed above the catalytic distillation zone to provide further purification of alkylbenzene. The overhead 102 or side draw above the catalyst bed is optionally subject to a hydrogen and/or water separation step to recover hydrogen and/or remove the dense water and optionally dried with drying agent such as molecular sieves, and alkylbenzene recovered can be recycled for reuse, or it can be returned to the distillation column at a point above the catalytic distillation zone as a reflux stream 111 for further purification. The de-watered overhead or side draw, optionally having water and hydrogen removed, comprises from about 90% to about 100%, particularly from about 98% to about 100% and more particularly from about 99.5% to about 100 percent by weight of alkylbenzene; from about 0% to about 10%, particularly from about 0% to about 5%, and more particularly from about 0% to about 1 percent by weight of alkylaryl alcohol, less than about 5%, particularly less than about 1%, more particularly less than about 0.1 percent by weight of alkenylbenzenes; less than about 5%, particularly less than about 1%, and more particularly less than about 0.1 percent by weight of dimers or oligomers of alkylbenzene; less than about 5%, particularly less than about 1%, and more particularly less than about 0.2 percent by weight of alkylcyclohexane.

Where a feed stream comprising cumyl alcohols is fed to the present catalytic distillation reactor, the overhead 102 or side draw above the catalyst bed, after the removal of water and/or hydrogen, comprises from about 90% to about 100%, particularly from about 98% to about 100% and more particularly from about 99.5% to about 100 percent by weight of cumene; from about 0% to about 10%, particularly from about 0% to about 5%, and more particularly from about 0% to about 1 percent by weight of cumyl alcohol, less than about 5%, particularly less than about 1%, more particularly less than about 0.1 percentage by weight of alpha-methyl styrene; less than about 5%, particularly less than about 1%, and more particularly less than about 0.1 percent by weight of dimers or oligomers of cumene; less than about 5%, particularly less than about 1%, and more particularly less than about 0.2 percent by weight of isopropylcyclohexane.

Without limiting the scope of the present invention, it is proposed that the mechanism that produces the effectiveness of the present process is the condensation of a portion of the alkylphenyl alcohol or alkenylbenzene-containing vapors in the reaction system, which occludes sufficient hydrogen in the condensed liquid to obtain the requisite intimate contact between the hydrogen and the alkenylbenzene, such as alpha-methyl styrene, in the presence of the catalyst to result in the hydrogenation of the side chains of alkenylbenzene.

As a particular embodiment, a reflux condenser is included in the system. The reflux ratio may vary over the rate of 1 to 20:1. In practice, the higher ratio may be used to compensate for a short catalyst bed. In commercial size units, the catalyst bed is normally provided with a lower reflux ratio and hence higher unit productivity is usually obtained.

The temperature in the reactor may be determined by the boiling point of the alkyl benzene at any given pressure. The distillation reactor may be operated at a pressure such that the reaction mixture is boiling in the bed of catalyst. Generally, pressures in the range of 0 psig to 400 psig may be employed, particularly from about 0 psig to about 140 psig (or about 1–10 bars).

For the conversion of a cumyl alcohol-containing feed stream, the pressure may be from about 0 psig to about 400 psig, particularly from about 5 psig to 300 psig, and more particularly from about 0 psig to about 140 psig (or about 1–10 bar). It is understood that cumene boils at about 152–154° C. at about 0 psig (1 bar), and at higher pressure, the boiling point of cumene will rise. As an illustrative non-limiting example, the present process operates at overhead pressure below 50 psig. Preferably, the reactor is operated at low pressure to reduce the temperature, thus preventing unwanted polymerization and achieving better selectivity. At about 0 psig (atmospheric pressure), the temperature at the bottom of the reactor is higher than about 200° C., and close to about 155° C. at the top, and about 150 to 210° C. in the catalytic distillation zone.

The feed weight hourly space velocity (WHSV), may vary over a very wide range within the other condition perimeters, and can be from about 0.1 hr$^{-1}$ to about 10 hr$^{-1}$, particularly from about 0.2 hr$^{-1}$ to about 2 hr$^{-1}$. WHSV, as used herein, means the unit weight of feed per hour entering the reaction distillation reactor per unit weight of catalyst in the reactor.

As an illustrative example, the feed stream contains from about 1% to about 100%, particularly from about 5% to about 75%, and more particularly from about 10% to about 40% by weight of alkyaryl alcohol; from about 0% to about 99%, particularly from about 25% to about 95%, and more particularly from about 60% to about 90% by weight of alkylbenzene; from about 0% to about 20%, particularly from about 0% to about 5%, and more particularly from about 0% to about 1% by weight of alkenylbenzene; and from about 0% to about 25%, particularly from about 0% to about 10%, and more particularly from about 0% to about 5% by weight of alkylbenzene hydroperoxide. As specific illustrative example of a particular embodiment of the present invention, the feed stream contains from about 1% to about 100%, particularly from about 5% to about 75%, and more particularly from about 10% to about 40% by weight of cumyl alcohol; from about 0% to about 99%, particularly from about 25% to about 95%, and more particularly from about 60% to about 90% by weight of cumene; from about 0% to about 20%, particularly from about 0% to about 5%, and more particularly from about 0% to about 1% by weight of alpha-methyl styrene; from about 0% to about 5 weight percent of ethyl benzene; from about 0% to about 5 weight percent of di-, tri-isopropyl benzene, ethyl benzene, propyl-benzene, ethyl-isopropyl benzene, etc., or mixtures thereof; and from about 0% to about 25%, particularly from about 0% to about 10%, and more particularly from about 0% to about 5% by weight of cumene peroxide.

Where a feed stream comprises a di-isopropyl benzene (DIPB), it might contain a small amount, e.g. less than 5% by weight, of cumene, tri-isopropyl benzene, ethyl benzene, propyl-benzene, ethyl-isopropyl benzene, etc., or mixtures thereof. This is also true for the streams which are cycled to peroxide, epoxidation, hydrogenation reactors, due to side reactions.

The hydrogenation rate should be adjusted such that it is sufficient to support the hydrogenation reaction and replace hydrogen lost from the catalyst. At least a stoichiometric amount of hydrogen relative to the alkenylbenzene (produced in transient before converted to alkylbenzene) should be present in the system to be available for the reaction. As a non-limiting example, a small excess of hydrogen flow is provided to occlude the hydrogen into the liquid and to accommodate the nature of this reaction between a gas and a liquid.

Hydrogenation carried out in a reactor for catalytic distillation requires only a fraction of the hydrogen partial pressure required in prior art liquid phase processes for this type of stream, but gives the same or better result. Thus, the capital investment and operating expense for the present hydrogenation process is substantially lower than prior art processes. The lower hydrogen partial pressures allow for the use of a more active catalyst at lower temperatures without unduly hydrogenating the aromatic part of the product.

The present catalytic distillation reaction also benefits from having the reaction occurring concurrently with distillation, the initial reaction products and other stream components are removed from the reaction zone as quickly as possible, reducing the likelihood of side reaction(s). Moreover, because all the components are boiling, the temperature of reaction is controlled by the boiling point of the mixture at the system pressure. The heat of reaction simply creates more boil-up but no increase in temperature at a given pressure. As a result, a great deal of control over the rate of reaction and distribution of products can be achieved by regulating the system pressure. Also, adjusting the throughput gives further control of product distribution and to a degree control of the side reactions such as dimerization and oligomerization. A further benefit that this reaction may gain from catalytic distillation is the washing effect that the internal reflux provides to the catalyst, thereby reducing polymer build up and coking of the catalyst. Internal reflux may vary over the range of 0.2–20 L/D (wt. liquid just below the catalyst bed/wt./distillate).

The catalytic material employed in the hydrogenation process also serves as distillation packing, i.e., it is a component of a distillation system functioning as both a catalyst and a distillation packing. The particulate catalyst material may be in any form, structure, size which provides sufficient surface area to allow a reasonable reaction rate. It may be a powder, small irregular chunks or fragments, or small beads and the like and compositions thereof. Non-limiting examples of the structure of the catalytic distillation beds include disposing particulate catalyst material within a porous plate or screen to contain the catalyst and provide distillation surfaces in the form of a wire mesh structure, such as a wire mesh tubular structure or any other similar structure. It may also be a flexible, semi-rigid open mesh tubular material, such as stainless steel wire mesh, filled with a particulate catalytic material. Specific examples of the catalyst structure can be found in U.S. Pat. Nos. 5,266,546, 4,242,530, 4,443,559, and 5,348,710, which are incorporated herein by reference in their entirety.

Any suitable hydrogenation catalyst may be used. As illustrative non-limiting examples, Group VIII metals of the Periodic Table of Elements are used as the principal catalytic component, alone or with promoters and modifiers such as palladium/gold, palladium/silver, cobalt/zirconium, nickel, preferably deposited on a support such as zeolite, alumina, fire brick, pumice, carbon, silica, thermally stable resin or the like. The catalysts contain from about 0.1% wt to about 5% wt, particularly from about 0.2% wt to 2% wt, calculated as the weight of the metal on the basis of the total weight of the catalyst, of Group VIII metal or a Group VIII metal compound supported on a carrier, particularly a zeolite. One illustrative example of a suitable catalytic material comprises palladium oxide or palladium, preferably 0.1% wt to 5.0% wt, supported on an appropriate support medium such as alumina, carbon, zeolite (such as mordenite) or silica. The gamma alumina supported copper based catalyst disclosed in U.S. Pat. No. 4,822,936, which is hereby incorporated by reference, may also be acceptable.

As other particular embodiments of the present invention, Group IB metals of the Periodic Table of Elements, such as copper, are used as the principle catalytic component, alone or with promoters and modifiers such as chromium, zinc, zirconium, Group VIII metals, etc. The Group IB metal-containing catalysts preferably contain from about 10% to about 80%, particularly from about 30% to about 70%, more particularly from about 50% to about 60%, as the weight of the oxide basis the total weight of the catalyst, of a Group IB metal, particularly on a support. Some specific illustrative examples include commercially available copper on silica catalyst, T-366 (having approximately 54 wt. % of copper on silica as a press extrudate or formed extrudate), obtainable from Sud Chemie; copper chromite catalyst, G-22/2, obtainable from Sud Chemie; and Cu/Zn/Zr catalyst prepared according Example 3 of U.S. Pat. No. 5,475,159, which is hereby incorporated by reference; and the like. Combinations of these catalysts may also be used. These catalysts are preferably reduced with dilute hydrogen in nitrogen before they are used.

The catalyst is subsequently reduced by hydrogen. The catalyst bed in the catalytic distillation zone may be prepared and pre-activated by the following non-limiting illustrative procedure. A catalyst is crushed and sized into appropriately sized, e.g. 6–20 mesh, particles. The catalyst is mixed with an inert diluent such as SiC and centered inside a stainless steel reactor tube between beds of 20 mesh SiC and isolated with glass wool to keep the catalyst(s) in place. The catalyst is slowly reduced by heating the catalyst particles to a temperature of e.g. about 150–250° C. at a rate of from about 1° C. to about 10° C., particularly from about 1.5° C. to about 5° C. per minute, while flowing about 0.001 to about 0.1, specifically about 0.02–0.10 wt. % hydrogen in nitrogen at a rate of 1–200, specifically 2–30 L/Hr. The catalyst is allowed to reduce at 150–250° C. for 1–10 hours and then the hydrogen content in the nitrogen is doubled every 1–5 hours until the gas is 1–10, specifically 2–5 wt. % hydrogen in nitrogen. The catalyst is reduced for a final one to five hour period and then cooled while maintaining gas flow. After cooling, the reactor is capped without allowing any air to enter and the gas flow is stopped. The reactor is opened in a nitrogen filled environment and the catalyst and silicon carbide are separated by screen sieve.

The 6–20 mesh particles of reduced catalyst, prepared by the afore-mentioned procedure, are loaded onto bed supports made of porous plate or screen in a distillation reactor in a nitrogen filled environment. Glass wool may also be used to support the catalyst particles. Hydrogen gas is added via a regulator to the apparatus to maintain a pressure between 0–450 psig, (typically between 0–150 psig). The flow rate is adjusted to maintain twice the amount of hydrogen required for the reaction stoichiometry. Feed stream containing alkyl alcohol, such as a stream containing (e.g. 10–40 weight %) of 2-phenyl-2-propanol (cumyl alcohol), is fed into the distillation reactor from below the catalyst beds. The bottom section of the distillation reactor is lowered into a heater and then the temperature is raised until the liquid refluxes in the distillation reaction zone containing the catalyst. Lower boiling alkylbenzenes, such as cumene, and water are distilled out from the top of the column. Additional alkyl alcohol, such as a cumyl alcohol-containing stream, is continually added with a slight molar excess of hydrogen to replace the amount of alkyl alcohol, such as cumyl alcohol, that is converted to alkylbenzene, such as cumene, and distilled off. The alkyl benzene, such as cumene product easily separates from the denser water phase. It is optionally dried further with molecular sieves or other suitable drying agents. The alkylbenzene, such as cumene, produced has a purity of more than 98 wt. %, preferably more than 99 wt. %. No measurable alkyl alcohol, such as cumyl alcohol (<0.01 wt. %) is found in the alkylbenzene, such as cumene product. When desired, the bottoms can be removed, optionally diluted with cumene and sent to a fixed bed hydrogenation reactor to make additional alkyl benzene, such as cumene.

The invention will be illustrated by the following illustrative embodiments which are provided for illustration purposes only and are not intended to limit the scope of the instant invention.

Illustrative and Comparative Embodiments

I. Illustrative Embodiment—Catalytic Distillation of Cumyl Alcohol to Cumene

IA. Preparation and Reduction of Catalyst—T-366

A commercially available copper on silica catalyst, T-366, available from Sud Chemie is further processed using the following procedure for the catalytic distillation mode experiments.

Five grams of Sud Chemie T-366 copper on silica catalyst (3 mm tablets) was crushed and sized into 6–20 mesh particles. The catalyst was mixed with 45 grams of 80 mesh silicon carbide and centered inside a 69 cm long stainless steel reactor tube between beds of 20 mesh SiC and glass wool. The reactor tube had an internal diameter of 1.5cm. The catalyst was slowly reduced by heating the catalyst particles at a rate of 3° C. per minute from 20° C. to 180° C. while flowing 0.05 wt. % hydrogen in nitrogen at a rate of 10 L/Hr. The catalyst was allowed to reduce at 180° C. for 2 hours and then the hydrogen content in the nitrogen was doubled every 2 hours until the gas was 3.2 wt. % hydrogen in nitrogen. The catalyst was reduced for a final two-hour period and then cooled while maintaining gas flow. After cooling, the reactor was capped without allowing any air to enter and the gas flow was stopped. The reactor was opened in a nitrogen filled glove box and the catalyst and silicon carbide were separated by screen sieve.

IB. Catalytic Distillation Using T-366 Catalyst

The 6–20 mesh particles of reduced T-366 catalyst, prepared by the procedure of Illustrative Embodiment I, were loaded into the reflux zone of a thick walled 31 cm long Vigreux column with an internal diameter of 1.5 cm while inside a nitrogen filled glove box. A small piece of glass wool was used to support the catalyst particles. The column was attached to a thick walled 250 ml round bottomed flask which served as the bottom segment of the reactor for catalytic distillation. Hydrogen gas was added via a regulator to the apparatus to maintain a pressure between 1 and 10 bar. The flow rate was adjusted to maintain twice the amount of hydrogen required for the reaction stoichiometry. 50 grams of 2-phenyl-2-propanol (cumyl alcohol) from Avacado Chemical was added to the 250 mL flask, containing a magnetic stir bar. The flask containing the cumyl alcohol was lowered into a heater and the temperature was raised until the liquid refluxed in the Vigreux column containing the catalyst. Lower boiling cumene and water were distilled out from the top of the column. Additional cumyl alcohol was continually added with a slight molar excess of hydrogen to replace the amount of cumyl alcohol that was converted to cumene and distilled off. The cumene product easily separated from the denser water phase. It was optionally dried further with 3 Å molecular sieves. The results are provided in Table 2 below. As shown, the top product stream produced, (after removal of the water), had a purity of cumene of >99.5 wt. %. No measurable cumyl alcohol (<0.01 wt. %) was found in the cumene product. When desired, the bottoms can be removed, optionally diluted with cumene and sent to a fixed bed hydrogenation reactor to make additional cumene.

TABLE 2

Results of Catalytic Distillation of Cumyl Alcohol to Produce Cumene - T-366

| Component | Feed | Top Product* |
| --- | --- | --- |
| 2-Phenyl-2-propanol, (wt %) | 99.2 | <0.1 |
| α-Methyl styrene, (wt %) | 0.4 | 0.2 |
| Cumene, (wt %) | 0.1 | >99.5 |
| Isopropylcyclohexane, (wt %) | 0.1 | 0.1 |
| Other, (wt %) | 0.2 | 0.1 |
| Cumene dimmer | <0.1 | Not detected |

*after removing the water produced

IC. Preparation of Pd-Mordenite Catalyst

A mixture of 1500 grams of sodium mordenite, (having the following properties: a surface area of 430 square meters per gram; an average crystallite size of around 1 micron; a cyclohexane adsorption uptake of 7.6 cc/g; and a molar silica to alumina ratio of 11.1), 9000 grams of ammonium nitrate and 15 liters of 1.5 M nitric acid was heated to 50° C. and stirred for five hours. The solid material was filtered off and washed with 25 liters of deionized water. This treatment of the Mordenite with ammonium nitrate in nitric acid was repeated twice with fresh ammonium nitrate and nitric acid each time. After each treatment the solid material was filtered off and washed with water and dried overnight at 120° C. Palladium was added to the zeolite to a level of 0.35 percent by weight by treatment with an aqueous solution containing Tetraamine palladium nitrate and an excess of ammonium nitrate prepared by dissolving 6.55 grams of tetramine palladium nitrate in 308 grams of deionized water and adding to this solution 4.92 grams of ammonium nitrate. The palladium solution was then co-mulled with 1083 grams of dealuminated mordenite having an LOI (loss of ignition at 750° C. for 2 hours) of 10.6%. The palladium-containing mordenite was uniformly mixed and then 338 grams of pseudoboehmite alumina (Catapal B which is commercially available from Vista Chemical Company) having an LOI of 28.4% was added and allowed to mix. The mixture was extruded and the 1.6 mm extrudates were dried in air for 16 hours at 125° C., and then calcined in flowing air at 500° C. for two hours. The catalyst was crushed and sized to 6–20 mesh particles and then further hydrogenated using the procedure as described in IA above for the catalytic distillation mode experiments.

ID. Catalytic Distillation Using Pd-Mordenite Catalyst

The reduced Pd-Mordenite catalyst, prepared by the procedure of Illustrative Embodiment IC above, was loaded into the reflux zone of a thick walled 31 cm long Vigreux column with an internal diameter of 1.5 cm while inside a nitrogen filled glove box. The same procedure as described in IB above was followed for the set-up and operation of a catalytic distillation operation. The results are provided in Table 3 below. As shown, the top product stream produced, after removal of water, had a purity of cumene of >99.5 wt. %. No measurable cumyl alcohol (<0.01 wt. %) was found in the cumene product. When desired, the bottoms can be removed, optionally diluted with cumene and sent to a fixed bed hydrogenation reactor to make additional cumene.

TABLE 3

Catalytic Distillation of 2-Phenyl-2-propanol - Results with Pd-Mordenite Catalyst

| Component | 2-Phenyl-2-propanol Feed | Catalytic Distillation Top Product* |
| --- | --- | --- |
| 2-Phenyl-2-propanol, (wt. %) | 99.2 | <0.1 |
| α-Methyl styrene, (wt. %) | 0.4 | Not Detected |
| Cumene, (wt. %) | 0.1 | >99.6 |
| Isopropylcyclohexane, (wt. %) | 0.1 | 0.2 |
| Cumene Dimer, (wt. %) | <0.1 | Not Detected |
| Other, (wt. %) | 0.2 | 0.1 |

*after removal of water

II. Comparative Embodiments—Fixed Bed Preparation of Cumene

IIA. Catalyst Containing Copper, Zinc and Zirconium

A catalyst was prepared according to Example 3 of U.S. Pat. No. 5,475,159, the description of Example 3 and for general preparation of catalysts in the specification are incorporated herein by reference.

IIB. Fixed Bed Conversion of Cumyl Alcohol to Cumene Using Catalyst Described in IIA 20.0 cc of the above Cu/Zn/Zr catalyst from IIA was crushed and sized into 6–20 mesh particles. The catalyst was mixed with 45 grams of 80 mesh silicon carbide and centered inside a 69 cm long stainless steel reactor tube between beds of 20 mesh SiC and glass wool. The reactor tube had an internal diameter of 1.5cm. The catalyst was slowly reduced by heating the catalyst particles at a rate of 3° C. per minute from 20° C. to 180° C. while flowing 0.05 wt. % hydrogen in nitrogen at a rate of 10 L/Hr. The catalyst was allowed to reduce at 180° C. for 2 hours and then the hydrogen content in the nitrogen was doubled every 2 hours until the gas was 3.2 wt. % hydrogen in nitrogen. The catalyst was reduced for a final two-hour period after which the gas was switched to 99.999% hydrogen and the reactor was pressurized with hydrogen to a gauge pressure of 290 psig (20 bar) while the catalyst bed was maintained at 180° C. The hydrogen flow rate was adjusted to 2 L/Hr.

A mixture containing about 25.5 wt. % of 2-phenyl-2-propanol (obtained from Avacado Chemical) and 74.5 wt % of cumene (obtained from Aldrich Chemical Co.) was fed the reactor at a feed rate of 33.5 g/hr. while maintaining the hydrogen flow rate and a bed temperature of 180° C. After a week of operation, a sample of the reactor product was collected, dried of water and analyzed by gas chromatography. The product contained 8.1 wt. % 2-phenyl-2-propanol, 91.2 wt. % of cumene, 0.1 wt. % alpha-methyl styrene, 0.1 wt. % of i-propylcyclohexane and 0.5 wt. % of cumene dimers.

IIC. Fixed Bed Conversion of Cumyl Alcohol to Cumene Using a Copper on Silica Catalyst The experiment of IIB was repeated using the copper on silica catalyst described in Example IB (T-366) obtained from Sud Chemie. 20 cc of the catalyst was used. Due to the higher activity of the reduced T-366 catalyst, the testing was conducted at a temperature of 150° C. After 200 hours of operation, the dried product contained 9.7 wt. % 2-phenyl-2-propanol, 88.4 wt. % of cumene, 0.1 wt. % alpha-methyl styrene, 0.1 wt. % of i-propylcyclohexane and 1.7 wt. % of cumene dimers. When operated at 180° C., the product contained less than 5 wt. % 2-phenyl-2-propanol.

IID. Preparation of Catalyst for Comparative Embodiments IIE 33.5 grams (20 cc) of a copper chromite catalyst (Sud Chemie G-22/2) was crushed and sized into 6–20 mesh particles. As before, the catalyst was mixed with 45 grams of 80 mesh silicon carbide and centered inside a 69 cm long stainless steel reactor tube between beds of 20 mesh SiC and glass wool. The reactor tube had an internal diameter of 1.5 cm. The catalyst was slowly reduced by heating the catalyst particles at a rate of 3° C. per minute from 20° C. to 180° C. while flowing 0.05 wt. % hydrogen in nitrogen at a rate of 10 L/Hr. The catalyst was allowed to reduce at 180° C. for 2 hours and then the hydrogen content in the nitrogen was doubled every 2 hours until the gas was 3.2 wt. % hydrogen in nitrogen. The catalyst was reduced for a final two hour period. The 3.2 wt. % hydrogen in nitrogen was replaced with hydrogen (>99.999%). After 2 hours, the reactor was pressurized with hydrogen to a gauge pressure of 290 psig (20 bar) while the catalyst bed was maintained at 180° C. The hydrogen flow rate was adjusted to 2 L/Hr.

IIE. Fixed Bed Conversion of Cumyl Alcohol to Cumene Using a Copper Chromite Catalyst A feedstock containing about 25 wt. % cumyl alcohol* (>98% purity, obtained from Avocado Chemical) in 75 wt. % cumene (>99% purity obtained from Aldrich Chemical) was made by blending. The hydrogenolysis reaction was conducted under the conditions provided in the Table 4 below. Two hydrogen flowrates were used during the testing, 2L/Hr or 4/Hr. The results of the testing are shown in Table 5 and Table 6. As demonstrated, this fixed bed process produces a cumene product stream of about 91 wt. % purity having 7.9 wt. % of unconverted cumyl alcohol, 0.6 wt. % of cumene dimers and 0.1 wt. % of isopropylcyclohexane as side products.

TABLE 4

Process Condition for Fixed Bed Conversion

| | |
|---|---|
| Feed rate | 33.5 g/hr (WHSV = 1.0 Hr$^{-1}$) |
| Reaction Temperature | 180° C. |
| Pressure | 20 bar |
| Hydrogen Flow rate | 2 L/Hr (or 4 L/Hr) |
| Catalyst Weight | 33.5 g (before reduction) |

TABLE 5

Fixed Bed Cumyl Alcohol to Cumene Results with G-22/2 Catalyst at 180° C. and a Hydrogen Flowrate of 4 L/Hr., After 800 Hours on Stream.

| Component | Feed | Product* |
|---|---|---|
| 2-Phenyl-2-propanol, (wt. %) | 24.8 | 7.9 |
| α-Methyl styrene, (wt. %) | 0.2 | <0.1 |
| Cumene, (wt. %) | 74.8 | 91.4 |
| Isopropylcyclohexane, (wt. %) | 0.1 | 0.1 |
| Cumene Dimer, (wt. %). | <0.1 | 0.6 |

*after removing the water produced

TABLE 6

Fixed Bed Cumyl Alcohol to Cumene Results with G-22/2 Catalyst at 180° C. and a Hydrogen Flowrate of 2 L/Hr., After 600 Hours on Stream

| Component | Feed | Product* |
|---|---|---|
| 2-Phenyl-2-propanol, (wt. %) | 24.8 | 8.9 |
| α-Methyl styrene, (wt. %) | 0.2 | <0.1 |
| Cumene, (wt. %) | 74.8 | 90.4 |
| Isopropylcyclohexane, (wt. %) | 0.1 | 0.1 |
| Cumene Dimer, (wt. %). | <0.1 | 0.6 |

*after removing the water produced

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant inventions defined by the instant specification and claims.

We claim:

1. A process for producing an alkylbenzene having the structure of $R_1R_2C(Ph)$ from an alkylphenyl alcohol having the structure $R_1R_2C(Ph)OH$ comprising the steps of:
   (a) feeding a feed stream comprising alkylphenyl alcohol having the structure $R_1R_2C(Ph)OH$ to a reactor having a catalytic distillation zone; and,
   (b) concurrently in the reactor:
      (i) contacting the feed stream comprising $R_1R_2C(Ph)OH$ with hydrogen in the catalytic distillation zone to convert $R_1R_2C(Ph)OH$ to $R_1R_2CH(Ph)$ and form a reaction mixture, and
      (ii) separating $R_1R_2CH(Ph)$ from the reaction mixture by fractional distillation to produce, at a position higher than the catalytic distillation zone, a stream comprising $R_1R_2CH(Ph)$ having a lower concentration of $R_1R_2C(Ph)OH$ than the feed stream from the reactor at a position higher than the catalytic reaction zone;
   wherein $R_1$ and $R_2$ each is hydrogen or a hydrocarbon group having 1–10 carbon atoms and at least one of $R_1$ and $R_2$ is not a hydrogen.

2. The process of claim 1, wherein less than 1.0% by weight of $R_1R_2C(Ph)$ OH in the feed stream is converted to $R_1R_2CH$.

3. The process as claimed in claim 1, wherein the alkylphenyl alcohol is selected from a group consisting of p-di(2-hydroxyl-2-propyl)benzene, m-di(2-hydroxyl-2-propyl)benzene, o-di(2-hydroxyl-2-propyl)benzene, 4-(2-hydroxy-2-propyl)cumene, 3-(2-hydroxy-2-propyl)cumene, 2-(2-hydroxy-2-propyl)cumene, and mixtures thereof.

4. The process of claim 1, wherein the alkylphenyl alcohol is ethylphenyl alcohol.

5. The process of claim 1, wherein in step (b), the feed stream is in contact with a catalyst comprising a Group VIII metal or a Group IB metal of the Periodic Table of Elements in the catalytic distillation zone.

6. The process of claim 1, wherein in step (b) the feed stream is in contact with a catalyst comprising palladium in the catalytic distillation zone.

7. The process of claim 1, wherein in step (b) the feed stream is in contact with a catalyst comprising copper in the catalytic distillation zone.

8. A process for producing cumene from 2-phenyl-2-propanol comprising the steps of:
  (a) feeding a feed stream comprising 2-phenyl-2-propanol to a reactor having a catalytic distillation zone; and,
  (b) concurrently in the distillation reactor
    (i) contacting the feed stream comprising 2-phenyl-2-propanol with hydrogen in the catalytic distillation zone to convert 2-phenyl-2-propanol to cumene and form a reaction mixture; and,
    (ii) separating cumene from the reaction mixture from (i) by fractional distillation to produce, at a position higher than the catalytic distillation zone, a stream comprising cumene and having a lower concentration of 2-phenyl-2-propanol than the feed stream.

9. The process of claim 8, wherein less than 0.5% wt of 2-phenyl-2-propanol in the feed stream is converted to i-propylcyclohexane.

10. The process of claim 8, wherein less than about 0.05% wt of the cumene produced in step (i) is converted to 2,3-dimethy-2,3-diphenyl butane or 2-methyl-2,4-diphenyl pentane.

11. The process of claim 8, wherein in step (b) the feed stream is in the presence of a catalyst comprising a group IB metal or a group VIII metal in the catalytic distillation zone.

12. The process of claim 8, wherein in step (b) the feed stream is in contact with a catalyst comprising palladium in the catalytic distillation zone.

13. The process of claim 8, wherein in step (b) the feed stream is in contact with a catalyst comprising copper in the catalytic distillation zone.

14. A process for producing cumene from 2-phenyl-2-propanol comprising the steps of:
  a. feeding a feed stream comprising 2-phenyl-2-propanol to a reactor comprising a distillation reaction zone;
  b. concurrrently in the reactor
    (i) contacting the feed stream comprising 2-phenyl-2-propanol with hydrogen in the presence of a catalyst comprising a group VIII metal or a group IB metal in the distillation reaction zone to convert 2-phenyl-2-propanol in the feed stream to cumene and form a reaction mixture comprising cumene;
    (ii) separating cumene from the reaction mixture by fractional distillation; and,
    (iii) withdrawing, at a position higher than the catalytic distillation zone, a stream comprising from about 98%wt to about 99.9% wt of cumene and having a lower concentration of 2-phenyl-2-propanol than the feed stream from the distillation column reactor;
  c. withdrawing from the reactor a bottom stream comprising 2-methyl-2,4-diphenylpentane and dimethyl-2,3-diphenylbutane from a position lower than the catalytic distillation zone; and,
  d. converting the 2-methyl-2,4-diphenylpentane and dimethyl-2,3-diphenylbutane in the bottom stream from (c) to cumene.

15. The process of claim 14, wherein in (b) (ii), less than about 0.5% wt of 2-phenyl-2-propanol is converted to i-propylcyclohexane.

16. The process of claim 14, wherein less than about 0.05% by weight of the cumene produced in step (b) (i) is converted to 2-methyl-2,4-diphenylpentane and dimethyl-2,3-diphenylbutane.

17. The process of claim 14, wherein in step (b)(i) the feed stream is in contact with a catalyst comprising palladium in the distillation reaction zone.

18. The process of claim 14, wherein in step (b)(i) the feed stream is in contact with a catalyst comprising copper in the distillation reaction zone.

* * * * *